United States Patent
Miles et al.

(10) Patent No.: US 6,576,459 B2
(45) Date of Patent: Jun. 10, 2003

(54) SAMPLE PREPARATION AND DETECTION DEVICE FOR INFECTIOUS AGENTS

(75) Inventors: Robin R. Miles, Danville, CA (US); Amy W. Wang, Oakland, CA (US); Christopher K. Fuller, Livermore, CA (US); Asuncion V. Lemoff, Union City, CA (US); Kerry A. Bettencourt, Dublin, CA (US); June Yu, Livermore, CA (US)

(73) Assignee: The Regents of the University of California, Oakland, CA (US)

(*) Notice: Subject to any disclaimer, the term of this patent is extended or adjusted under 35 U.S.C. 154(b) by 215 days.

(21) Appl. No.: 09/815,624

(22) Filed: Mar. 23, 2001

(65) Prior Publication Data

US 2002/0137196 A1 Sep. 26, 2002

(51) Int. Cl.[7] .................................................. C12M 1/36
(52) U.S. Cl. ........................ 435/286.5; 435/286.7; 435/287.2; 435/288.5; 435/288.7; 435/810; 435/962
(58) Field of Search .......................... 435/286.5, 286.7, 435/287.2, 288.5, 288.7, 810, 962

(56) References Cited

U.S. PATENT DOCUMENTS

| | | | | |
|---|---|---|---|---|
| 5,436,129 A | * | 7/1995 | Stapleton | 435/6 |
| 5,486,335 A | * | 1/1996 | Wilding et al. | 422/55 |
| 5,639,428 A | * | 6/1997 | Cottingham | 422/112 |
| 6,054,277 A | * | 4/2000 | Furcht et al. | 435/6 |
| 6,126,804 A | * | 10/2000 | Andresen | 204/601 |
| 6,184,029 B1 | * | 2/2001 | Wilding et al. | 435/287.1 |
| 6,372,484 B1 | * | 4/2002 | Ronchi et al. | 435/287.2 |

* cited by examiner

Primary Examiner—David A. Redding
(74) Attorney, Agent, or Firm—L. E. Carnahan; Eddie E. Scott; Alan H. Thompson

(57) ABSTRACT

A sample preparation and analysis device which incorporates both immunoassays and PCR assays in one compact, field-portable microchip. The device provides new capabilities in fluid and particle control which allows the building of a fluidic chip with no moving parts, thus decreasing fabrication cost and increasing the robustness of the device. The device can operate in a true continuous (not batch) mode. The device incorporates magnetohydrodynamic (MHD) pumps to move the fluid through the system, acoustic mixing and fractionation, dielectrophoretic (DEP) sample concentration and purification, and on-chip optical detection capabilities.

19 Claims, 1 Drawing Sheet

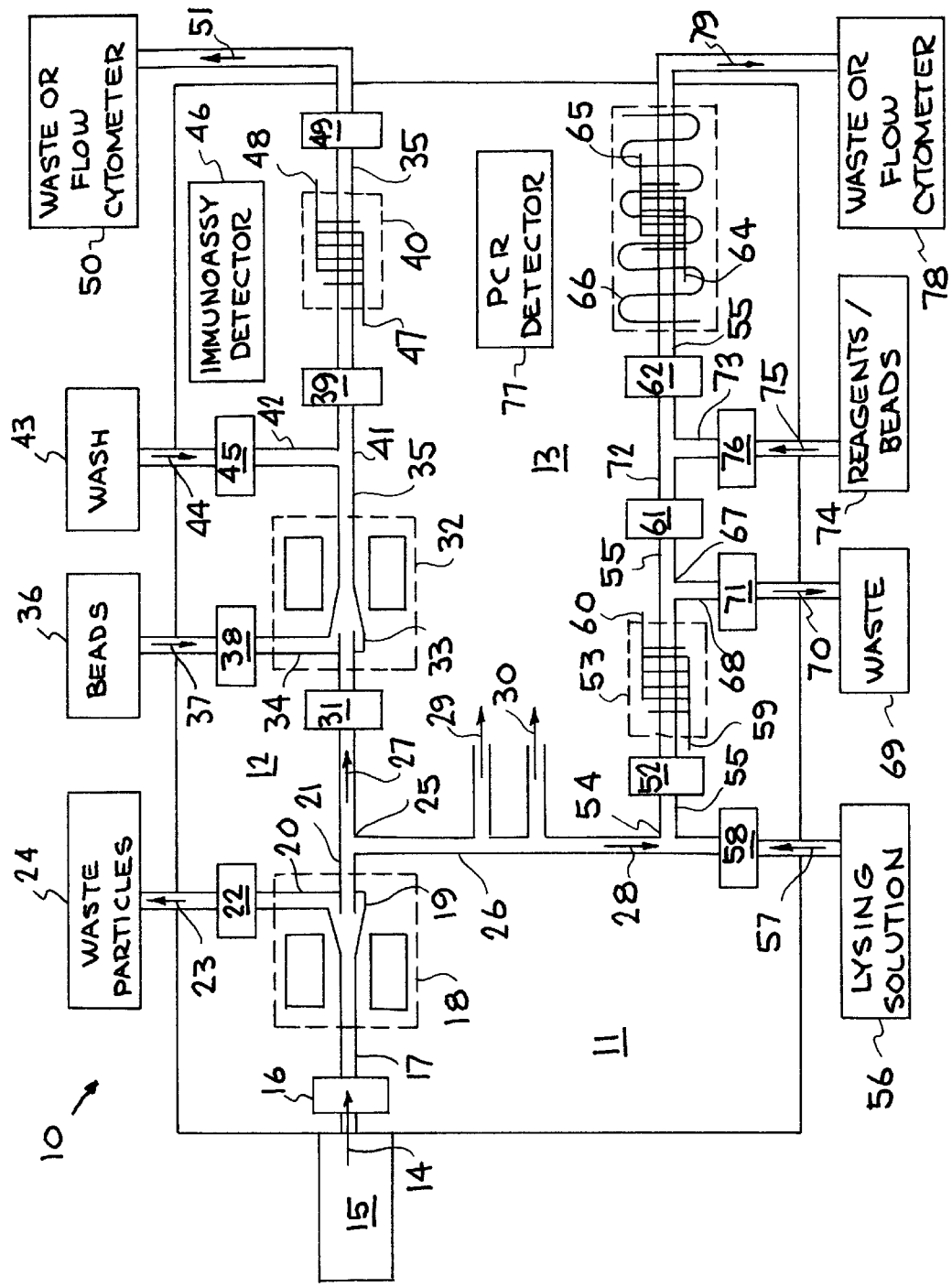

SAMPLE PREPARATION AND DETECTION DEVICE FOR INFECTIOUS AGENTS

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to microfluidic devices, particularly to sample preparation and detection devices, and more particularly to a sample preparation and analysis to which may incorporate both immunoassays and PCR assays in one compact, field-portable microchip.

Microfluidic systems are becoming increasingly popular as a way to integrate sample preparation and biological assays on a single substrate. The resulting reduction in manual operations and reduced reagent use can lead to significant cost savings in performing biological tests.

Whether in defense of bioterrorists or checking a blood sample of a potential victim, there is a need for field-portable biodetectors. Many microfluidic chips have been proposed for PCR/DNA analysis and for immunoassays. However, there is no known approach that incorporates both types of diagnostics on a single chip. The ability to perform multiple diagnostics on a single substrate is important in many counter biological warfare applications to reduce the rate of false positives. Current commercial microdevices concentrate on the assay over the sample preparation because the expected user is usually a highly skilled laboratory technician.

The present invention involves a single biochip having the capability of performing both immunoassays and PCR assays. This feature is important when a device needs to run multiple inexpensive, specific tests. The immunoassays are relatively inexpensive for use in multiple tests and yet often inaccurate, while PCR tests can be very specific and can be used to verify the results of the immunoassay. The immunoassays can be run in true continuous mode with the device of the present invention; the device can be monitoring a significant amount of fluid continuously checking for a positive signal; and the overall sensitivity of the device can be orders of magnitude greater than other microdevices.

SUMMARY OF THE INVENTION

It is an object of the present invention to provide for sample preparation and analysis in one field-portable microchip.

A further object of the invention is to provide for both immunoassays and PCR assays in one compact, field-portable microchip.

Another object of the invention is to provide a fluidic microchip having capabilities for fluid and particle control with or without moving parts.

Another object of the invention is to provide a sample preparation and analysis tool that can operate in a true continuous mode.

Another object of the invention is to provide a field-portable microchip for sample preparation and analysis which includes micro-pumps, such as magnetohydrodynamic pumps, acoustic mixing and fractionation, dielectrophoretic sample concentration and purification, and on-chip optical detection capabilities.

Other objects and advantages of the present invention will become apparent from the following description and accompanying drawings. Basically, the present invention comprises a sample preparation and detection device for applications such as detecting the presence of pathogens in a bio-terrorist event or to sample blood for the presence of infectious agents. The sample preparation and analysis device can be located in one compact, field-portable microchip. The device of this invention is incorporates both immunoassays and PCR assays, can have no moving parts, and can operate in a continuous mode. The single microchip, for example may contain no moving parts and include a micro-pumps, such as magnetohydrodynamic (MHD) pumps to move the fluid through the system, acoustic mixing and fractionation, dielectrophoretic (DEP) sample concentration and purification, and have on-chip optical detection capabilities, thereby providing inexpensive and robust instrumentation. Unlike other devices such as capillary electrophersis which require that all sample be introduced in a small volume at a single time for analysis, the device of the present invention can continuously monitor a fluid volume checking for a positive signal. The device is also capable of concentrating the sample into a smaller volume, inherently increasing the sample concentration and improving the overall sensitivity of the microdevice over those only capable of fluid handling. In this way, the overall sensitivity of the device can be greater than any known microdevice.

BRIEF DESCRIPTION OF THE DRAWINGS

The accompanying drawing, which is incorporated into and forms a part of the disclosure, illustrates an embodiment of the invention and, together with the description, serves to explain the principles of the invention.

The single FIGURE illustrates an embodiment of the sample preparation and analysis device of the invention which incorporates both immunoassays and PCR assays in one compact, field portable microchip.

DETAILED DESCRIPTION OF THE INVENTION

The present invention involves a sample preparation and analysis device with or without moving parts for fluid and particle control, and which may incorporate both immunoassays and PCR assays in one compact, field-portable microchip. The device is unique in that it can operate in a true continuous (not batch) mode, and incorporates many features on the microfluidic chip including micro-pumps, such as magnetohydrodynamic (MHD) pumps, to move the fluid through the device, acoustic mixing and fractionation, dielectrophoretic (DEP) sample concentration and purification, and on-chip optical detection capabilities, which result in an inexpensive, robust instrumentation. The device can be used to detect the presence of pathogens, such as spores, in a bio-terrorist event or to sample blood for the presence of infectious agents.

The invention provides the ability to perform multiple diagnostics on a single substrate as is important in many counter biological warfare applications to reduce the rate of false positives. The biochip of this invention is capable of performing both immunoassays and PCR assays. This feature is important when a device needs to run multiple inexpensive, specific tests. The immunoassays are relatively inexpensive for use in multiple tests and yet often inaccurate. PCR tests can be very specific and can be used to verify the results of the immunoassay. Unlike other test devices, the device of this invention can be monitoring a significant amount of fluid such as (several tens of ml) continuously checking for a positive signal. As a result, the overall sensitivity of the device can be greater than currently known microdevices.

The present invention results from developing unique MEMS technologies to perform the fluidic functions of mixing, concentration, purification, pumping and switching. Novel acoustic methods are used to provide separation ad mixing functions, dielectrophoretic (DEP) particle capture is used to concentrate and purify the samples, and micropumps, such as magnetohydrodynamic (MHD) pumps are used as a means of pumping and switching the fluid through flow channels in the system. All devices preferably have no moving parts.

A non-contact method of manipulating particles in a plastic, glass, or polymeric microfluidic chamber employing acoustic radiation pressure has been demonstrated. Fluidic chambers conducive to producing acoustic mixing of 1–10 $\mu$m-sized polystyrene and glass beads have been developed. Piezoelectric transducers are driven at half wavelength resonance frequencies to provide best mixing results. Mixing speed increases with drive voltage. Pulsed drive voltages have also been used to induce mixing in microfluidic channels. Increased binding of antibodies to bead surfaces in the presence of acoustic mixing has been demonstrated. Also acoustic forces for concentration of particles is being employed, and concentration of polystyrene particles in a generated pressure node of the acoustic field has been demonstrated.

The system of the present invention involves a dielectrophoretic (DEP) concentrator. The dielectrophoretic force results from the ability of a particle to become polarized in the presence of a non-uniform electric field. Particles in the field will be attracted to areas of high or low field gradient depending on its electrical properties relative to those of the suspending medium. This force is highly dependent on the electrical properties of both the suspending medium and the particles. The capture of spores, DNA, bacterial cells, and polystyrene beads using dielectrophoresis has been demonstrated. Typical devices consisted of 30 $\mu$m electrode width and spacing platinum electrodes fabricated on glass with $5V_{rms}$ applied voltage. Biologicals and beads were trapped along the edges of the interdigitated electrodes at the regions of high field gradient. It was found that DNA trapping was easiest at lower frequencies between 100 Hz to 1 kHz. At frequencies below 500 Hz bubble nucleation due to hydrolysis limited the excitation voltage. Bacillus Globigii spores and Erwinia Herbicola bacteria were effectively captured by the field at frequencies ranging from 1 kHz to 3 Mhz. Polystrene beads were captured only a very low frequencies. The effect of flow velocity on trapping efficiency on biologicals has also been examined.

The system of this invention utilized magnetohydrodynamic (MHD) or other micro pumping and switching. An AC MHD pump and switch, which makes use of the Lorentz force to move an ionic solution has been demonstrated. Electrodes were microfabricated down the sidewalls of a silicon-glass-silicon sandwich device, and a perpendicular magnetic field was generated from an external AC magnet below the device. Salt solutions (NaCl) down to 0.01M produced pumping motion. The direction of pumping motion can be controlled by the relative phase between the magnetic and electric drive signals. Integration of two AC MHD pumps into a Y-shaped fluidic circuit has been shown to produce a fluidic switch.

Based on the above referenced demonstrated acoustic mixing, dielectrophoretic concentrating, and MHD pumping, the combination of these features into the system or device described hereinafter and illustrated in the drawing provides a complete sample preparation and analysis to which incorporates both immunoassays and PCR assays in one compact, field-portable microchip.

An embodiment of the device or system of the present invention is shown in the single figure and comprises three sections, a sample preparation section, an immunoassay section, and a PCR passage section. While the samples of the illustrated system are shown to be derived from a compact, high efficiency aerosol collector, they could equally well originate from a swab sample or from blood or tissue samples where the cause of an infection is being sought. The second component in the system is an ultrasonic fractionation or filtering device which is sensitive to density and size differences between particles. Large particles and dense particles will be transferred to waste. This component will also help break up clumps of spores and other agglomerations to facilitate antibody-based assays. The particles discharging from the component into the system can be subjected to either an immunoassay or a PCR assay. As seen, the fluid flow through the system is carried out by a number of MHD pumps. The first component in the immunoassay leg of the system in an ultrasonic mixer where antibody-coated beads are introduced and mixed with the pathogenic particles. The beads can be held in place use a dielectrophoretic (DEP) force in a DFP bead concentrator while they are washed to enhance the subsequent detection. The beads can be checked for the presence of pathogens by detecting the antigen-antibody binding when held by the dielectrophoretic force by interdigitated electrodes in the DEP bead concentrator or they can be passed to waste or to an external flow cytometer for analysis. The particles from the ultrasonic filtering component could instead go to the PCR assay leg of the system where they will be collected and concentrated by dielectrophoretic force and then used in the DEP concentration/purification components. Again, the lysing solution and the sample particles are moved through the system by MHD pumps. The DNA will move to a second set of electrodes in amplification/concentration components which includes a thin-film heater in preparation for PCR amplification and detection of the DNA from the pathogens. A Taqman assay can be used and the fluorescent signal detected in real-time or they can be attached to beads and passed to waste or to an external flow cytometer for analysis.

Referring now to the single figure, an embodiment of the invention is shown which comprises a system or device generally indication at 10 located on a single compact, field-portable microchip 11 and includes an immunoassay section 12 and a PCR assay section 13. Sample containing pathogenic particles indicated by arrow 14 is moved from a collector or other source 15 by an MHD pump 16 through a microchannel 17 into an ultrasonic fractionation or filtering assembly generally indicated at 18 and which is sensitive to density and size differences between particles. Microchannel 17 terminates in a separator 19 with microchannels 20 and 21 extending from separator 19. Microchannel 20 is directed through a MHD pump 22 and carries large particles and dense particles indicated by arrow 23, which are transferred to waste as indicated at 24. Microchannel 21 includes a function 25 from which extends a microchannel 26, with microchannel 21 supplying sample to immunoassay section 12 as indicated by arrow 27 and microchannel 26 supplying sample to PCR assay section 13 for DNA analysis, as indicated by arrow 28. Components 14–24 constitute a sample preparation section of device 10. As indicated by dash lines and arrows 29 and 30 additional immunoassay legs can be connected to microchannel 26. Sample in microchannel 21 is moved by an MHD pump 31 into an ultrasonic bed mixing assembly generally indicated at 32, and the sample is directed into a mixer 33 from which extend microchannels 34 and 35. Antibody coated beads 36 are moved as indicated by arrow 37 by an MHD pump 38 through microchannel 34 into mixed 33 for mixing with sample from microchannel 21 wherein certain of the pathogenic particles in the sample attach to the beads 36, and the particle attached beads and remaining sample are moved from mixer 33 via microchannel 35 by an MHD pump 39 toward a DEP bead concentration assembly generally indicated at 40. Microchannel 35 includes a junction 41 for connection to a microchannel 42 by which a wash 43 is moved as indicated by arrow 44 by an MHD pump 45 through microchannel 42 into microchannel 35 for washing the particle attached beads to enhance the subsequent detection. The beads can, if necessary, be held in place along microchannel 35 for washing by use of dielectrophoretic force. As the beads pass through the DEP bead concentration assembly 40, the beads are checked by immunoassay detector 46 for the presence of pathogens by detecting the antigen-antibody binding when held by the dielectrophoretic force produced by interdigitated electrodes 47 and 48, or they can be passed through assembly 40 via microchannel 35 by a MHD pump 49 to a waste 50 or an external flow cytometer for analysis, as indicated by arrow 51.

Part of the sample with pathogenic particles from separator 19 as moved into the PCR assay section 13 through microchannel 26 by an MHD pump 52 into a DEP concentration/purification assembly 53 via a junction 54 and microchannel 55. A lysing solution 56 is moved as indicated by arrow 57 by an MHD pump 58 into microchannel 26 and is mixed with the sample in microchannel 55 and assembly 53 for lysing the pathogenic particles in the sample, the particles being concentrated by DEP forces produced by interdigitated electrodes 59 and 60 of assembly 53. The DNA will move through microchannel 55 via MHD pumps 61 and 62 to an amplification/concentration assembly 63 containing interdigitated electrodes 64 and 65 and a thin film heater 66 in preparation for PCR amplification and detection of the DNA from pathogens. Between assemblies 53 and MHD pump 61 microchannel 55 is provided with a junction 67 and microchannel 68 by which waste 69 is moved as indicated by arrow 70 via an MHD pump 71. Between MHD pumps 61 and 62 microchannel 55 is provided with a junction 72 from which a microchannel 73 extends and through which reagents/bead 74 are moved as indicated by arrow 75 via an MHD pump 76 into microchannel 55 and into assembly 63 via MHD pump 62 for processing of the DNA by PCR analysis. The DNA is detected by a PCR detector 77 as it passes through assembly 63. A Taqman assay, for example, is used and the fluorescent signals detected in real-time, or they can be attached to beads and passed to an external flow cytometer for analysis or to waste 78 as indicated by arrow 79.

It has thus been shown that the present invention enables both immunoassays and PCR assays to be carried out in one compact, field-portable microchip. This is accomplished with or without moving parts thus decreasing fabrication costs and increasing the robustness of the device, as well as enabling operation in a continuous (not batch) mode. The device of this invention can be used, for example, to detect the presence of pathogens, such as spores, in a bio-terrorist event or to sample blood for the presence of infectious agents.

While a particular embodiment of the invention has been illustrated and described, along with particular applications for the invention, such are not intended to be limiting. Modifications and changes may become apparent to those skilled in the art and it is intended that the invention be limited only by the scope of the appended claims.

What is claimed is:

1. A sample preparation and analysis device, comprising:
   a microchip, and
   a microfluidic system formed on said microchip, said microfluidic system including a sample preparation section, and at least one of an immunoassay section, and a PCR assay section,
   said immunoassay section and said PCR assay section being constructed to receive sample from said sample preparation section.

2. The device of claim 1, wherein said sample preparation section includes an ultrasonic fractionation and filtering assembly.

3. The device of claim 2, wherein said preparation assembly include a separator, said separator being operatively connected to receive sample, to discharge sample waste, and to discharge sample for assay.

4. The device of claim 3, wherein said separator is operatively connected to a plurality of pumps, selected from the group consisting of micro-pumps and MHD pumps, for moving sample into and for discharging sample from said separator.

5. The device of claim 2, wherein said preparation assembly is constructed to be sensitive to density and size differences between particles.

6. The device of claim 3, wherein said separator of said preparation assembly is constructed to transfer large particles and dense particles to waste via a micro-pump or a MHD pump.

7. The device of claim 2, wherein said preparation assembly is constructed to break up clumps of spores and other agglomeration to facilitate antibody-based assays.

8. The device of claim 1, wherein said immunoassay section includes an ultrasonic bead mixing assembly constructed to receive sample from said sample preparation section and to receive antibody-coated beads, and includes a mixer for mixing said sample and said beads.

9. The device of claim 8, wherein said mixing assembly is provided with a plurality of MHD pumps for moving said sample and said beads into said mixer.

10. The device of claim 8, wherein said immunoassay section also includes a DEP bead concentration assembly.

11. The device of claim 10, wherein said concentration assembly includes a plurality of interdigitated electrodes for producing a dielectrophoretic force for concentrating said antibody-coated beads.

12. The device of claim 10, additionally including means for washing said antibody-coated beads located intermediate said mixing assembly and said concentration assembly and including a plurality of MHD pumps for moving a wash material and for moving the washed beads into the concentration assembly.

13. The device of claim 10, additionally including a detector positioned adjacent said concentration assembly for determining the presence of pathogens in the sample by detecting the antigen-antibody binding as sample passes through said concentration assembly.

14. The device of claim 1, wherein said PCR assay section includes a DEP concentration/purification assembly constructed to receive DNA containing sample from said sample preparation section and to receive a lysing solution, and a plurality of MHD pumps to move said lysing solution and DNA containing sample into said concentration/purification assembly.

15. The device of claim 14, wherein said PCR assay section additionally includes an amplification/concentration assembly and a plurality of MHD pumps for moving sample from said concentration/purification assembly and reagents/beads from a source into said amplification/concentration assembly.

16. The device of claim 14, additionally including a MHD pump for moving sample from said concentration/purification assembly to waste.

17. The device of claim 14, wherein each of said concentration/purification assembly include a plurality of interdigitated electrodes for producing a dielectrophoretic force.

18. The device of claim 17, wherein said amplification/concentration assembly additionally includes a heater unit.

19. The device of claim 14, additionally including a PCR detector located adjacent the amplification/concentration assembly.

* * * * *